US005905069A

United States Patent [19]
Borsook et al.

[11] Patent Number: 5,905,069
[45] Date of Patent: May 18, 1999

[54] METHODS OF DECREASING OR PREVENTING PAIN USING SPICAMYCIN OR DERIVATIVES THEREOF

[75] Inventors: David Borsook, Concord; Jeffrey William Clark, Chestnut Hill, both of Mass.

[73] Assignee: The General Hospital Corporation, Boston, Mass.

[21] Appl. No.: 09/013,711

[22] Filed: Jan. 26, 1998

[51] Int. Cl.$^6$ ..................................................... A61K 31/70
[52] U.S. Cl. ............................................................ 514/45
[58] Field of Search ......................................... 514/45, 46

[56] References Cited

U.S. PATENT DOCUMENTS

| 5,461,036 | 10/1995 | Otake et al. | 514/46 |
| 5,631,238 | 5/1997 | Otake et al. | 514/45 |

FOREIGN PATENT DOCUMENTS

| 0 525 479 A1 | 2/1993 | European Pat. Off. |
| WO 90/15811 | 12/1990 | WIPO |

OTHER PUBLICATIONS

Kamishohara et al., "Antitumor Activity of SPM VIII, A Derivative of the Nucleoside Antibiotic Spicamycin, Against Human Tumor Xenografts", The Journal of Antibiotics 47:1305–1311, 1994.

Kamishohara et al., "Antitumor Activity of a Spicamycin Derivative, KRN5500, and its Active Metabolite in Tumor Cells", Oncology Research 6:383–390, 1994.

Kamishohara et al., "Inhibitory Effect of a Spicamycin Derivative, KRN5500, on the Growth of Hepatic Metastasis of Human Colon Cancer–Producing . . . ", Cancer Chemother Pharmacol 38:495–498, 1996.

Kamishohara et al., "Structure–Antitumor Activity Relationship of Semi–Synthetic Spicamycin Analogues", The Journal of Antibiotics 46:1439–1446, 1993.

Sakai et al., "Structure–antitumor Activity Relationship of Semi–synthetic Spicamycin Derivatives", The Journal of Antibiotics 48:1467–1488, 1995.

Sakai et al., "Synthesis and Antitumor Activities of Glycine–exchanged Analogs of Spicamycin", The Journal of Antibiotics 48:504–508, 1995.

Simpson et al., "Reduction in the Mechanonociceptive Response by Intrathecal Administration of Glycine and Related Compounds", Neurochemical Research 21:1221–1226, 1996.

Simpson et al., "Reduction in Thermal Hyperalgesia by Intrathecal Administration of Glycine and Related Compounds", Neurochemical Research 22:75–79, 1997.

Woolf, "The Pathophysiology of Peripheral Neuropathic Pain — Abnormal Peripheral Input and Abnormal Central Processing", Acta Neurochir 58:125–130, 1993.

*Primary Examiner*—William R. A. Jarvis
*Attorney, Agent, or Firm*—Fish & Richardson P.C.

[57] ABSTRACT

Methods of providing pain relief which includes the steps of identifying an animal in need of pain relief and administering an amount of spicamycin or a derivative thereof sufficient to provide pain relief.

21 Claims, No Drawings

METHODS OF DECREASING OR PREVENTING PAIN USING SPICAMYCIN OR DERIVATIVES THEREOF

BACKGROUND OF THE INVENTION

This invention relates to a method of decreasing or preventing pain.

Spicamycin (SPM) is an antitumor antibiotic produced by the bacterium *Streptomyces alanosinicus* 879-MT$_3$ (Hayakawa et al., Agric Biol Chem 49:2685–2691 [1985]). The naturally occurring compound has the following general structure, varying solely in the fatty acid moiety:

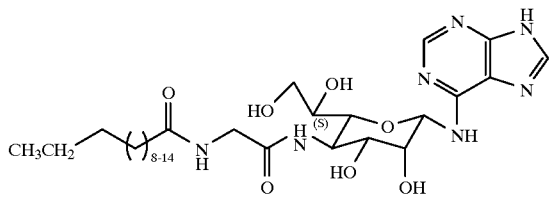

Formula I: Spicamycin

Synthetic variants of spicamycin and their use as an antitumor agent is described in Otake et al., U.S. Pat. Nos. 5,461,036 and 5,631,238.

SUMMARY OF THE INVENTION

The invention is based on the unexpected discovery that administration of a spicamycin derivative to a patient suffering from pain resulted in a significant decrease of that pain. Thus, the invention features a method of providing pain relief by identifying an animal in need of pain relief and then administering to the animal an amount of a compound which is a spicamycin derivative (Formula II), e.g., KRN5500 (6-[4-deoxy-4-[(2E,4E)-tetradecadienoylglycyl] amino-L-glycero-β-L-manno heptopyranosyl]amino-9H-purine) (Formula III) as shown below.

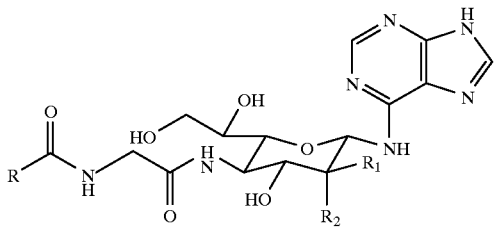

Formula II: Spicamycin Derivative wherein $R_1$ and $R_2$ are different from each other and represent H or OH, and R represents a substituted or unsubstituted alkyl.

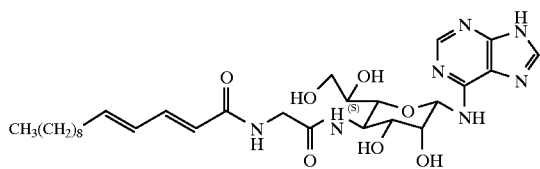

Formula III: KRN5500

The term "alkyl" denotes a straight or branched hydrocarbon chain containing carbon atoms or cyclic hydrocarbon moieties. These alkyl groups may also contain one or more double bonds or triple bonds. By "substituted alkyl" is meant an alkyl in which an atom of the alkyl is substituted with, for example, a sulphur, oxygen, or halogen atom.

An "animal in need of pain relief" does not necessarily experience pain currently, and "pain relief" includes less than 100% reduction in pain.

For example, the invention can be used to treat an animal, including a human patient, for neuropathic pain attributable to any cause. Examples include postherpetic neuralgia, phantom or amputation stump pain, diabetic neuropathy, acquired immune deficiency syndrome neuropathy, back pain, and visceral pain (e.g., chronic pancreatitis). By "neuropathic pain" is meant pain arising from injury to or disturbance of the peripheral nervous system.

The compound can be administered locally or systemically, e.g. via an implant (for slow release, for example) or by intravenous bolus injection or infusion.

An "implant" is any device residing in a tissue deeper than the skin in which the device produces a regulated or continuous release of a compound.

Treatment in accordance with the invention produces relief of pain in patients whose current pain is resistant to other methods of pain relief, such as the use of opioid drugs. The invention can also be used in anticipation of pain to prevent pain.

Unless otherwise defined, all technical and scientific terms used herein have the same meaning as commonly understood by one of ordinary skill in the art to which this invention belongs. Although suitable methods and materials are described below, methods and materials similar or equivalent to those described herein can be used in the practice or testing of the present invention. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention is based on the discovery that administration of a spicamycin derivative to a human patient suffering from pain resulted in a significant decrease of that pain. The pain-relieving and pain-preventing properties of SPM or derivatives thereof are here shown for the first time.

Various spicamycin derivatives have been synthesized which vary in the specific $R_1$, $R_2$, and R groups (U.S. Pat. Nos. 5,461,036 and 5,631,238). In one variation $R_1$ is H and $R_2$ is OH, while in another variation, $R_1$ is OH and $R_2$ is H. Each variation contains a R group that results in, but is not limited by, the following compounds and salts thereof:

6-[4'-N-(N'-tridecanoylglycyl)spicaminyl-amino]purine (SPM 9),
6-[4'-N-(N'-tetradecanoylglycyl)spicaminyl-amino]purine (SPM 10),
6-[4'-N-(N'-10-methylundecanoylglycyl)spicaminyl-amino] purine (SPK 9),
6-[4'-N-(N'-11-methyldodecanoylglycyl)spicaminyl-amino] purine (SPK 251),
6-[4'-N-(N'-12-methyltridecanoylglycyl)spicaminyl-amino] purine (SPK 136),
6-[4'-N-(N'-11-dodecenoylglycyl)spicaminyl-amino]purine (SPK 44),
6-[4'-N-(N'-12-tridecenoylglycyl)spicaminyl-amino]purine (SPK 142),
6-[4'-N-(N'-cis-9-tetradecenoylglycyl)spicaminyl-amino] purine (SPK 231), 6-[4'-N-(N'-cis-9-hexadecenoylglycyl)spicaminyl-amino]
purine (SPK 148),
6-[4'-N-(N'-trans-2-dodecenoylglycyl)spicaminyl-amino]
purine (SPK 86),
6-[4'-N-(N'-trans-2-tetradecenoylglycyl)spicaminyl-amino]
purine (SPK 156),
6-[4'-N-(N'-trans-2-hexadecenoylglycyl)spicaminyl-amino]
purine (SPK 188),
6-[4'-N-(N'-trans,trans-2,4-dodecadienoyl-glycyl)
spicaminyl-amino]purine (SPK 282),
6-[4'-N-(N'-trans,trans-2,4-tridecadienoyl-glycyl)
spicaminyl-amino]purine (SPK 281),
6-[4'-N-(N'-trans,trans-2,4-tetradecadienoyl-glycyl)
spicaminyl-amino]purine (SPK 241),
6-[4'-N-(N'-11-bromoundecanoylglycyl)spicaminyl-amino]
purine (SPK 64),
6-[4'-N-(N'-12-bromododecanoylglycyl)spicaminyl-amino]
purine (SPK 152),
6-[4'-N-(N'-13-bromotridecanoylglycyl)spicaminyl-amino]
purine (SPK 276),
6-[4'-N-(N'-14-bromotetradecanoylglycyl)spicaminyl-
amino]purine (SPK 273),
6-[4'-N-(N'-12-chlorododecanoylglycyl)spicaminyl-amino]
purine (SPK 132),
6-[4'-N-(N'-13-chlorotridecanoylglycyl)spicaminyl-amino)
purine (SPK 278),
6-[4'-N-(N'-14-chlorotetradecanoylglycyl)spicaminyl-
amino]purine (SPK 280),
6-[4'-N-(N'-14-fluorotetradecanoylglycyl)spicaminyl-
amino]purine (SPK 279),
6-[4'-N-(N'-15-fluoropentadecanoylglycyl)spicaminyl-
amino]purine (SPK 247),
6-[4'-N-(N'-16-fluorohexadecanoylglycyl)spicaminyl-
amino]purine (SPK 157),
6-[4'-N-(N'-11-iodoundecanoylglycyl)spicaminyl-amino]
purine (SPK 165),
6-[4'-N-(N'-2-chlorohexadecanoylglycyl)spicaminyl-
amino]purine (SPK 135),
6-[4'-N-(N'-2-fluorododecanoylglycyl)spicaminyl-amino]
purine (SPK 159),
6-[4'-N-(N'-2-fluorohexadecanoylglycyl)spicaminyl-amino]
purine (SPK 233),
6-[4'-N-(N'-2,2-difluorotetradecanoylglycyl)-spicaminyl-
amino]purine (SPK 182),
6-[4'-N-(N'-2-hydroxyhexadecanoylglycyl)spicaminyl-
amino]purine (SPK 112),
6-[4'-N-(N'-(S)-2-hydroxyhexadecanoylglycyl)-spicaminyl-
amino]purine (SPK 271),
6-[4'-N-(N'-(R)-3-hydroxytetradecanoylglycyl)-spicaminyl-
amino]purine (SPK 270),
6-[4'-N-(N'-(S)-3-hydroxytetradecanoylglycyl)-spicaminyl-
amino]purine (SPK 274),
6-[4'-N-(N'-3-hydroxyhexadecanoylglycyl)-spicaminyl-
amino]purine (SPK 115),
6-[4'-N-(N'-16-cyanohexadecanoylglycyl)-spicaminyl-
amino]purine (SPK 177),
6-[4'-N-(N'-11-phenoxyundecanoylglycyl)-spicaminyl-
amino]purine (SPK 422),
6-[4'-N-(N'-12-phenoxydodecanoylglycyl)-spicaminyl-
amino]purine (SPK 249),
6-[4'-N-(N'-(R)-2-acetoxyhexadecanoylglycyl)-spicaminyl-
amino]purine (SPK 198),
6-[4'-N-(N'-3-acetoxyhexadecanoylglycyl)-spicaminyl-
amino]purine (SPK 189),
6-[4'-N-(N'-12-butanesulfonyloxydodecanoylglycyl)-
spicaminyl-amino]purine (SPK 232),
6-{4'-N-[N'-11-(2'-thienyl)-10-undecynoylglycyl]-
spicaminyl-amino}purine (SPK 262),
6-{4'-N-[N'-11-(3'-thienyl)-10-undecynoylglycyl]-
spicaminyl-amino}purine (SPK 263), and
6-{4'-N-[N'-11-(3'-furyl)-10-undecynoylglycyl]-
spicaminyl-amino}purine (SPK 266).
6-[4'-N-(N'-tridecanoylglycyl)spicaminyl-amino]purine
(SPM 9),
6-[4'-N-(N'-tetradecanoylglycyl)spicaminyl-amino]purine
(SPM 10),
6-[4'-N-(N'-10-methylundecanoylglycyl)spicaminyl-amino]
purine (SPK 9),
6-[4'-N-(N'-11-methyldodecanoylglycyl)spicaminyl-amino]
purine (SPK 251),
6-[4'-N-(N'-12-methyltridecanoylglycyl)spicaminyl-amino]
purine (SPK 136),
6-[4'-N-(N'-11-dodecenoylglycyl)spicaminyl-amino]purine
(SPK 44),
6-[4'-N-(N'-12-tridecenoylglycyl)spicaminyl-amino]purine
(SPK 142),
6-[4'-N-(N'-cis-9-tetradecenoylglycyl)spicaminyl-amino]
purine (SPK 231),
6-[4'-N-(N'-cis-9-hexadecenoylglycyl)spicaminyl-amino]
purine (SPK 148),
6-[4'-N-(N'-trans-2-dodecenoylglycyl)spicaminyl-amino]
purine (SPK 86),
6-[4'-N-(N'-trans-2-tetradecenoylglycyl)spicaminyl-amino]
purine (SPK 156),
6-[4'-N- (N'-trans-2-hexadecenoylglycyl)spicaminyl-amino]
purine (SPK 188),
6-[4'-N-(N'-trans,trans-2,4-dodecadienoylglycyl)
spicaminyl-amino]purine (SPK 282),
6-[4'-N-(N'-trans,trans-2,4-tridecadienoylglycyl)
spicaminyl-amino]purine (SPK 281),
6-[4'-N-(N'-trans,trans-2,4-tetradecadienoylglycyl)
spicaminyl-amino]purine (SPK 241),
6-[4'-N-(N'-11-bromoundecanoylglycyl)spicaminyl-amino]
purine (SPK 64),
6-[4'-N-(N'-12-bromododecanoylglycyl)spicaminyl-amino]
purine (SPK 152),
6-[4'-N-(N'-13-bromotridecanoylglycyl)spicaminyl-amino]
purine (SPK 276),
6-[4'-N-(N'-14-bromotetradecanoylglycyl)spicaminyl-
amino]purine (SPK 273),
6-[4'-N-(N'-12-chlorododecanoylglycyl)spicaminyl-amino]
purine (SPK 132),
6-[4'-N-(N'-13-chlorotridecanoylglycyl)spicaminyl-amino)
purine (SPK 278),
6-[4'-N-(N'-14-chlorotetradecanoylglycyl)spicaminyl-
amino]purine (SPK 280),
6-[4'-N-(N'-14-fluorotetradecanoylglycyl)spicaminyl-
amino]purine (SPK 279),
6-[4'-N-(N'-15-fluoropentadecanoylglycyl)spicaminyl-
amino]purine (SPK 247),
6-[4'-N-(N'-16-fluorohexadecanoylglycyl)spicaminyl-
amino]purine (SPK 157),
6-[4'-N-(N'-11-iodoundecanoylglycyl)spicaminyl-amino]
purine (SPK 165),
6-[4'-N-(N'-2-chlorohexadecanoylglycyl)spicaminyl-
amino]purine (SPK 135),
6-[4'-N-(N'-2-fluorododecanoylglycyl)spicaminyl-amino]
purine (SPK 159),
6-[4'-N-(N'-2-fluorohexadecanoylglycyl)spicaminyl-amino]
purine (SPK 233),
6-[4'-N-(N'-2,2-difluorotetradecanoylglycyl)spicaminyl-
amino]purine (SPK 182),
6-[4'-N-(N'-2-hydroxyhexadecanoylglycl)spicaminyl-
amino]purine (SPK 112),
6-[4'-N-(N'-(S)-2-hydroxyhexadecanoylglycyl)-spicaminyl-
amino]purine (SPK 271), 6-[4'-N-(N'-(R)-3-hydroxytetradecanoylglycyl)-spicaminyl-amino]purine (SPK 270),
6-[4'-N-(N'-(S)-3-hydroxytetradecanoylglycyl)-spicaminyl-amino]purine (SPK 274),
6-[4'-N-(N'-3-hydroxyhexadecanoylglycyl)-spicaminyl-amino]purine (SPK 115),
6-[4'-N-(N'-16-cyanohexadecanoylglycyl)-spicaminyl-amino]purine (SPK 177),
6-[4'-N-(N'-11-phenoxyundecanoylglycyl)-spicaminyl-amino]purine (SPK 422),
6-[4'-N-(N'-12-phenoxydodecanoylglycyl)-spicaminyl-amino]purine (SPK 249),
6-[4'-N-(N'-(R)-2-acetoxyhexadecanoylglycyl)-spicaminyl-amino]purine (SPK 198),
6-[4'-N-(N'-3-acetoxyhexadecanoylglycyl)-spicaminyl-amino]purine (SPK 189),
6-[4'-N-(N'-12-butanesulfonyloxydodecanoylglycyl)-spicaminyl-amino]purine (SPK 232),
6-{4'-N-[N'-11-(2'-thienyl)-10-undecynoylglycyl]-spicaminyl-amino}purine (SPK 262),
6-{4'-N-[N'-11-(3'-thienyl)-10-undecynoylglycyl]-spicaminyl-amino}purine (SPK 263), and
6-{4'-N-[N'-11-(3'-furyl)-10-undecynoylglycyl]-spicaminyl-amino}purine (SPK 266).

Neuropathic pain is pain derived from a lesion or disorder of the peripheral nervous system (reviewed in Woolf, Acta Neurochir 58:125–130 [1993]). Patients with neuropathic pain typically present with a characteristic set of sensory disorders independent of the cause, including a constant scalding or burning pain, a partial loss of sensitivity, tactile or cold allodynia, or hyperpathia to repeated stimulation. Experiments using the Randall-Selitto or Bennet Xie rat models for pain have shown that glycine release leads to a reduction of neuropathic pain (see Simpson, Jr. et al. [1996] Neurochem Res 21:1221–1226 and Simpson, Jr. et al. [1997] Neurochem Res 22:75–79). Thus, the pain relieving activity of spicamycin derivatives may, at least in part, rely on the glycly moiety linking the alkyl group to the sugar.

Peripheral neuropathic pain includes a number of diverse conditions, the commonest of which are trigeminal neuralgia, postherpetic neuralgia, painful diabetic neurophathy, and the reflex sympathetic dystrophies including causalgia, mononeuropathies, and peripheral nerve injury.

Few non-surgical alternatives exist for a patient with a disabling pain resistant to opioid drugs. The method of this invention provides alternatives to such patients.

The compound of the present invention can be administered via any appropriate route, e.g. intravenously, intraarterially, topically by injection, intraperitoneally, intrapleurally, orally, subcutaneously, intramuscularly, sublingually, intraepidermally, or rectally. It can be formulated as a solution, suspension, suppository, tablet, granules, powder, capsules, ointment, or cream. In the preparation of these pharmaceuticals, a solvent (e.g., water or physiological saline), solubilizing agent (e.g., ethanol, Polysorbates, or Cremophor EL®), agent for making isotonicity, preservative, antioxidizing agent, excipient (e.g., lactose, starch, crystalline cellulose, mannitol, maltose, calcium hydrogen phosphate, light silicic acid anhydride, or calcium carbonate), binder (e.g., starch, polyvinylpyrrolidone, hydroxypropyl cellulose, ethyl cellulose, carboxy methyl cellulose, or gum arabic), lubricant (e.g., magnesium stearate, talc, or hardened oils), or stabilizer (e.g., lactose, mannitol, maltose, polysorbates, macrogols, or polyoxyethylene hardened castor oils) can be added. If necessary, glycerin, dimethylacetamide, 70% sodium lactate, a surfactant, or a basic substance such as sodium hydroxide, ethylenediamine, ethanolamine, sodium bicarbonate, arginine, meglumine, or trisaminomethane is added. Pharmaceutical preparations such as solutions, tablets, granules or capsules can be formed with these components.

The dose of the compound of the present invention is determined in consideration of the results of animal experiments and various conditions. More specific doses obviously vary depending on the administration method, the condition of the subject such as age, body weight, sex, sensitivity, food eaten, dosage intervals, medicines administered in combination, and the source, seriousness, and degree of pain. The optimal dose and the administration frequency under a given condition must be determined by the appropriate dosage test of a medical specialist based on the aforementioned guide.

This invention will be further described in the following examples, which do not limit the scope of the invention described in the claims.

EXAMPLE 1

Treating a Patient Experiencing Neuropathic Pain with KRN5500

A patient with a 10 year history of chronic pain from peripheral nerve damage due to Reynaud's phenomenon developed liver cancer and was treated at Massachusetts General Hospital (MGH), Boston, Mass. The patient gave written consent to MGH for treating his liver cancer with KRN5500, a spicamycin derivative.

KRN5500 was adminstered to the patient as a daily one hour infusion via a central intravenous catheter for 5 consecutive days every 21 days. 0.80 mg of KRN5500 in saline was administered during each one hour infusion. The patient experienced pain relief within one hour after the initial administration.

It should be noted that, although the patient experienced pain relief from the intravenous dosage of KRN5500 described above, any other effective dose combined with any other effective method of administration can be used. For example, 1 ng to 4 mg/m$^2$ body surface area, or more preferably 80 ng to 1 mg/m$^2$ body surface area can be administered intravenously each day when pain relief is required. The effective dosages and methods of administration can be easily determined by one skilled in the art.

What is claimed is:

1. A method of providing pain relief, said method comprising the steps of:
   (a) identifying an animal in need of pain relief; and
   (b) administering to said animal an amount of a compound of Formula II effective to provide significant pain relief in the animal,

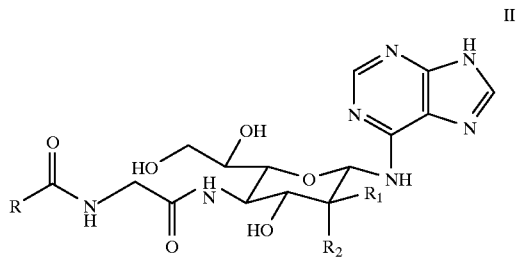

wherein $R_1$ and $R_2$ are different from each other and represent H or OH, and R represents a substituted or unsubstituted alkyl.

2. The method of claim 1, wherein R of Formula II is selected from the group consisting of:

(1) a linear alkenyl having 11–13 carbon atoms;
(2) a linear, unsubstituted alkyl having 11–13 carbon atoms and no double or triple bonds;
(3) a linear haloalkyl having 10–15 carbon atoms;
(4) $CH_3(CH_2)_nCH(OH)$— or $CH_3(CH_2)_{n-1}CH(OH)CH_2$—, wherein n denotes an integer from 9–13;
(5) an alkyl having 10–15 carbon atoms substituted with an azide group or a cyano group;
(6) a linear alkyl having 10–13 carbon atoms substituted with a phenoxy group or a halogen-substituted phenoxy group;

(7)
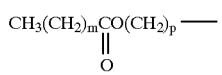

wherein m denotes an integer from 0–2 and p denotes an integer from 9–14;

(8)
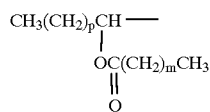

wherein m denotes an integer from 0–2 and p denotes an integer from 8–13;

(9)
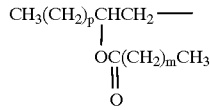

wherein m denotes an integer from 0–2 and p denotes an integer from 10–15;

(10) $CH_3(CH_2)_mSO_2O(CH_2)_p$—, wherein m denotes an integer from 0–3 and p denotes an integer from 9–14;

(11)
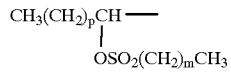

wherein m denotes an integer from 0–3 and p denotes an integer from 10–15;

(12)
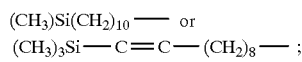

(13)
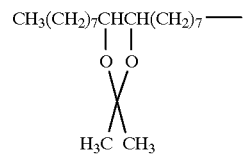

(14)
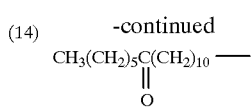

(15)
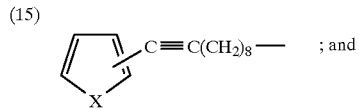
; and

(16) a linear alkadienyl having 11–13 carbon atoms.

3. The method of claim 1, wherein R of Formula II is selected from the group consisting of:
(1) a linear alkenyl having 11–13 carbon atoms;
(2) a linear, unsubstituted alkyl having 11–13 carbon atoms and no double or triple bonds; and
(3) $CH_3(CH_2)_nCH(OH)$— or $CH_3(CH_2)_n$—$CH(OH)CH_2$—, wherein n denotes an integer from 9–13.

4. The method of claim 1, wherein R of Formula II is an alkadienyl having 11 carbon atoms.

5. The method of claim 1, wherein R of Formula II is an alkadienyl having 12 carbon atoms.

6. The method of claim 1, wherein R of Formula II is an alkadienyl having 13 carbon atoms.

7. The method of claim 1, wherein $R_1$ is H and $R_2$ is OH.

8. The method of claim 6, wherein $R_1$ is H and $R_2$ is OH.

9. The method of claim 1, wherein the compound is 6-[4-deoxy-4-[(2E,4E)-tetradecadienoylglycyl]amino-L-glycero-β-L-manno heptopyranosyl]amino-9H-purine.

10. The method of claim 1, wherein said pain is neuropathic.

11. The method of claim 9, wherein said pain is postherpetic neuralgia, phantom or amputation stump pain, diabetic neuropathy, acquired immune deficiency syndrome neuropathy, back pain, visceral pain, or chronic pancreatitic neuropathy.

12. The method of claim 1, wherein said pain is opioid-resistant.

13. The method of claim 1, wherein said animal is a human.

14. The method of claim 1, wherein said compound is administered locally at the site of pain.

15. The method of claim 1, wherein said compound is administered systemically.

16. The method of claim 1, wherein said compound is administered via an implant.

17. The method of claim 16, wherein said implant provides slow release of said compound.

18. The method of claim 1, wherein said compound is administered intravenously.

19. The method of claim 1, wherein said compound is administered to the animal prior to the expected onset of pain.

20. The method of claim 1, wherein the amount administered is 1 ng to 4 mg/m$^2$ patient body surface area.

21. The method of claim 1, wherein the amount administered is 80 ng to 1 mg/m$^2$ patient body surface area.

* * * * *